United States Patent
Mitragotri et al.

[11] Patent Number: 6,018,678
[45] Date of Patent: Jan. 25, 2000

[54] TRANSDERMAL PROTEIN DELIVERY OR MEASUREMENT USING LOW-FREQUENCY SONOPHORESIS

[75] Inventors: Samir S. Mitragotri, Cambridge; Daniel Blankschtein, Brookline; Robert S. Langer, Newton, all of Mass.

[73] Assignee: Massachusetts Institute of Technology, Cambridge, Mass.

[21] Appl. No.: 08/545,236

[22] Filed: Oct. 19, 1995

Related U.S. Application Data

[60] Division of application No. 08/511,583, Aug. 4, 1995, and a continuation-in-part of application No. 08/152,442, Nov. 15, 1993, Pat. No. 5,458,140.

[51] Int. Cl.[7] ........................................ A61N 1/30
[52] U.S. Cl. .................................. 604/20; 604/22
[58] Field of Search .................... 424/450, 489; 604/20, 22

[56] References Cited

U.S. PATENT DOCUMENTS

| | | | |
|---|---|---|---|
| 3,661,864 | 5/1972 | Marschlar | 424/7 |
| 3,711,602 | 1/1973 | Horschler | 424/46 |
| 3,711,608 | 1/1973 | Horschler | 424/243 |
| 4,002,221 | 1/1977 | Buchalter | 181/0.6 |
| 4,127,128 | 11/1978 | Tokomoto et al. | 128/172.1 |
| 4,144,648 | 3/1979 | Takamoto et al. | 32/40 R |
| 4,176,664 | 12/1979 | Kalish | 128/158 |
| 4,249,531 | 2/1991 | Hiller et al. | 128/260 |
| 4,280,494 | 7/1981 | Cosgrove, Jr., et al. | 128/213 R |
| 4,309,989 | 1/1982 | Fahlm | 128/24 A |
| 4,372,296 | 2/1983 | Fahlm | 128/24 A |
| 4,537,776 | 8/1985 | Cooper | 514/424 |
| 4,557,943 | 12/1985 | Rosler et al. | 427/38 |
| 4,563,184 | 1/1986 | Korol | 604/368 |
| 4,646,725 | 3/1987 | Moasset | 128/24 A |
| 4,698,058 | 10/1987 | Greenfeld et al. | 604/266 |
| 4,767,402 | 8/1988 | Kost | 604/22 |
| 4,780,212 | 10/1988 | Kost et al. | 210/646 |

(List continued on next page.)

FOREIGN PATENT DOCUMENTS

| | | | |
|---|---|---|---|
| 0 043738 B1 | 10/1985 | European Pat. Off. | A61K 9/06 |
| 0368408 | 5/1990 | European Pat. Off. | |
| 386408 A2 | 5/1990 | European Pat. Off. | |
| 0612525 | 8/1994 | European Pat. Off. | |
| 612525 A1 | 8/1994 | European Pat. Off. | |
| 27 56 460 A1 | 6/1979 | Germany | A61M 37/00 |
| 3-170172 | 7/1991 | Japan | A61N 1/30 |
| 445433 | 11/1974 | U.S.S.R. | |
| 556805 | 6/1977 | U.S.S.R. | |
| 591186 | 1/1978 | U.S.S.R. | |
| 0910157 | 2/1978 | U.S.S.R. | |
| 506421 | 2/1978 | U.S.S.R. | |
| 1 577 661 | 2/1976 | United Kingdom | |
| 2153223 | 8/1985 | United Kingdom | A61K 47/00 |
| 88/0000 | 11/1988 | WIPO | |
| 90/0197 | 8/1990 | WIPO | |
| 90/01971 | 8/1990 | WIPO | |
| 91/12772 | 9/1991 | WIPO | A61B 17/00 |
| 93/20745 | 10/1993 | WIPO | A61B 6/00 |

OTHER PUBLICATIONS

Apfal R.E., "Possibility of Microcavisation from Diagnostic Ultrasound" IEEE Trans. Ultrason Forroelectics Froq Control UFFC 33:139–142 (1986).

(List continued on next page.)

*Primary Examiner*—Gollamudi S. Kishore
*Attorney, Agent, or Firm*—Arnall Golden & Gregory, LLP

[57] ABSTRACT

Applications of low-frequency (20 KHz) ultrasound enhances transdermal transport of high-molecular weight proteins. This method includes a simultaneous application of ultrasound and protein on the skin surface in order to deliver therapeutic doses of proteins across the skin. Examples demonstrate in vitro and in vivo administration of insulin (molecular weight 6,000 D), and in vitro administration of gamma interferon (molecular weight 17,000 D), and erythropoeitin (molecular weight 48,000 D).

7 Claims, 2 Drawing Sheets

U.S. PATENT DOCUMENTS

| | | | |
|---|---|---|---|
| 4,787,888 | 11/1988 | Fox | 604/20 |
| 4,820,720 | 4/1989 | Sanders et al. | 514/356 |
| 4,821,740 | 4/1989 | Tachibana et al. | 128/798 |
| 4,834,978 | 5/1989 | Nuwayser | 424/448 |
| 4,855,298 | 8/1989 | Yamada et al. | 514/259 |
| 4,860,058 | 8/1989 | Kobayashi et al. | 355/27 |
| 4,863,970 | 9/1989 | Patel et al. | 514/784 |
| 4,953,565 | 9/1990 | Tachibana et al. | 128/798 |
| 5,006,342 | 4/1991 | Cleary et al. | 424/445 |
| 5,007,438 | 4/1991 | Tachibana et al. | 128/798 |
| 5,016,615 | 5/1991 | Driller | 128/24 A |
| 5,076,273 | 12/1991 | Schoendorfer et al. | 128/632 |
| 5,115,805 | 5/1992 | Bommannan et al. | 128/24 AA |
| 5,139,023 | 8/1992 | Stanley et al. | 128/637 |
| 5,140,985 | 8/1992 | Schroder et al. | 128/632 |
| 5,171,215 | 12/1992 | Flanagan | 604/22 |
| 5,197,946 | 3/1993 | Tachibana | 604/22 |
| 5,231,975 | 8/1993 | Bommannan et al. | 128/24 AA |
| 5,267,985 | 12/1993 | Shimada et al. | 604/290 |
| 5,315,998 | 5/1994 | Tachibana et al. | 128/660.01 |
| 5,323,769 | 6/1994 | Bommanan | 601/2 |
| 5,386,837 | 2/1995 | Sterzer . | |
| 5,401,237 | 3/1995 | Tachibana et al. | 604/4 |
| 5,405,614 | 4/1995 | D'Angelo et al. | 424/449 |
| 5,415,629 | 5/1995 | Henley . | |
| 5,421,816 | 6/1995 | Lipkovker | 604/20 |
| 5,445,611 | 8/1995 | Eppstein et al. | 604/49 |
| 5,458,140 | 10/1995 | Eppstein | 128/632 |
| 5,469,856 | 11/1995 | Ungen | 128/662.02 |

OTHER PUBLICATIONS

Aungst, et al., "Contributions of Drug Solubilization Partitioning, Barrier Disruption and Solvent Parmeation to the Enhancement of Skin Permeation of Various Compounds with Fatty Acids and Aminos," *Pharm. Res.* 7:712–718 (1990).

Barry, "Mode of Action of Penetration Enhancers in Human Skin," *J. Controlled Rel.* 6:85–97 (1987).

Egorov, E.A. et al., "Use of the Variants of the Pharmacophysical Influence in Opthalmology", 102 Ophthalmology Journal #2 (1992).

Eppstein, D.A. et al., "Applications of Liposome Formulations for Antimicrobial/Antiviral Therapy" Liposomes as Drug Carriers 311, 315 (G. Gregoriadis ed. 1988).

Eppstein, D.A., "Medical Utility of Interferons: Approaches to Increasing Therapeutic Efficacy" 7 Pharmacy International 195–198 (1986).

Eppstein, D.A. et al., "Alternative Delivery Systems for Peptides and Proteins as Drugs" 5 CRC Reviews in Therapeutic Drug Carrier Systems 99, 125 (1988).

Loshilov, V.I. et al., "Research of the Technological Process of Ultrasound Treatment of Infected Wounds" (1976).

Ulashik, V.S. et al., Ultrasound Therapy (Minsk, Belarus 1983).

Prausnitz, et al., "Electroportion of mammalian skin: A mechanism to enhance transdermal drug delivery," *Proc. Natl. Acad. Sci.USA* 90:10504–10508 (1993).

Quillen, W.S., "Phonophoresis: A Review of the Literature and Technique," *Athl. Train.* 15:109–110 (1990).

Robinson & Lee, "Influence of Drug Properties on Design," *Controlled Drug Delivery* 42–43.

Rosell, J., et al., "Skin Impedance From 1 Hz to 1 MHz," *IEEE Trans. Biomed. Eng.* 35:649–651 (1988).

Skauen, et al., "Phonophoresis," *Int. J. Pharm.* 20:235–245 (1984).

Stringfellow, Clinical Applications of interferons and their inducers, (Editors, Marcel Dekker, New York, 1986).

Tamada, et al., *Proceed. Intern. Symp. Control. Rel. Bioact. Mater.* 22, 129–130 (1995).

Tocanne, et al., "Lipid lateral diffusion and membrane organization," *FEB* 257:10–16 (1989).

Tyle and Agrawala, "Drug Delivery by Phonophoresis," *Pharm. Res.* 6:355–361 (1989).

Veillard, et al., "Buccal Controlled Delivery of Peptides," *Proceed. Intern. Symp. Control. Rel. Biact. Mater (Controlled Release Society, Inc.)* 14:6 (1987).

Walker and Hadgraft, "Oleic acid—a membrane 'fluidiser' or fluid within the membrane," *Int. J. Pharm.* 71:R1–R4 (1991).

Walmsely, "Applications of Ultrasound in Dentistry," *Ultrasound in Med. and Biol.* 14:7–14 (1988).

Walters, K. A., "Penetration Enhancers and Their Use in Transdermal Therapeutic Systems," *Transdermal Drug Delivery: Developmental Issues and Research Initiatives*, 197–246 (Hadgraft J., Guy, R.H., Editors, Marcel Dekker, 1989).

Wester and Mailbach, "Animal Models for Percutaneous Absorption," Topical Drug Bioavailability Bioequivalence and Penetration (Shah and Maibach, Editors, Plenum Press, New York) 333–349, (1993).

Wheatley, et al., "Use of Ussing Chamber for Investigation of Drug Delivery Across Viable Nasal Tissue Membranes," *Proceed. Intern. Symp. Control. Rel. Bioact. Mater.* (Controlled Release Society, Inc. 14:26–27 (1987).

Williams, et al., "On the non–Guassian distribution of human skin permeabilities," *Int. J. Pharm.* 86:69–77 (1992).

Wilschut, et al., "Estimating Skin Permeation, The Validation of Five Mathematical Skin Permeation Models," *Chemosphere* 30:1275–1296 (1995).

Mezei Topics in Pharmaceutical Science, p. 345, 1985.

Eggerth, et al., "Evaluation of Hamster Cheek Pouch as a Model for Buccal Absorption," *Proceed. Intern. Symp. Rel. Bioact. Mater.*, (Controlled Release Society, Inc.) 14:180–181 (1987).

D'Emanuele, et al., "An Investigation of the Effects of Ultrasound on Degradable Polyanhydride Matrices," *Macromolecules* 25:511–515 (1992).

Elias, "The Microscopic Structure of the Epidermis and Its Derivatives," *Percutaneous Absorption: Mechanisms–Methodology–Drag Delivery* (Bronaugh, R.L., Mailbach, H., Editors, Marcel Dekker, New York,) 1–12 (1989).

Flynn, G. L., "Mechanism of Percutaneous Absorption from Physicochemical Evicence," Percutaneous Absorption: Mechanisms–Methodology–Drug Delivery (Bronaugh, R. L., Mailbach, H., Editors, Marcel Dekker, New York) 27–51 (1989).

Friedman, R. M., 'Interferons: A Primer', (Academic Press, New York, 1981).

Gaertner, W., "Frequency Dependence of Ultrasonice Cavitation," *J. Acoust. Soc. Am.* 26:977–980 (1954).

Ghanem et al., "The effects of ethanol on the transport of lipophilic and polar permeants across hairless mouse skin: Methods/validation of a novel approach," *Int. J. Pharm.* 78:137–156 (1992).

Grups and Frohmuller, "Cyclic Interferon Gamma Treatment of Patients with Metastatic Renal Carcinoma," *J. Med.* 64(3):218–220 (1989).

Hansch and Leo, "Substitutent Constants for Correlation Analysis in Chemistry and Biology" (1979).

Junginger, et al., "Visualization of Drug Transport Across Human Skin and the Influence of Penetration Enhancers," *"Drug Permeation Enhancement"* (Hsieh, D.S., Editors, Marcel Dekker, Inc. New York) 59–89 (1994).

Kasting, et al., "Prodrugs for Dermal Delivery: Solubility, Molecular Size, and Functional Group Effects," Prodrugs: Topical and Ocular Delivery Sloan, ed. (Marcel Dekker, NY 1992) 117–161.

Kost and Langer, "Ultrasound–Mediated Transdermal Drug Delivery," *Topical Drug Bioavailability Bioequivalence and Penetration* (Maibach, H. I., Shah, V. P., Editors, Plenum Press, New York) 91–104 (1993).

Kost, et al., "Ultrasound Effect of Transdermal Drug Delivery," (Ben Gurion University Dept. of Chem. Engineering, Beer Sheva Israel) (MIT, Dept. of Applied Biological Sciences, Cambridge, MA) CRS Aug. 1986.

Krall, L.P., 'World Book of Diabetes in Practice' (Editors, Elsvier, 1988).

Lee, V. H. L., et al., "Protease Inhibition as an Additional Mechanism for the Nasal Absorption Enhancement Effect of Sodim Taurodihydrofusidate," *Proceed. Intern. Symp. Control. Rel. Bioact. Mater* 14:55–56 (1987).

Lee, V. H. L.,. et al., "Nasal Peptide and Protein Absorption Promotors: Aminopeptidase Inhibition as a Predictor of Absorption Enhancement Potency of Bile Salts," *Proceed. Intern. Symp. Control. Rel. Bioact. Mater* 14:53–54 (1987).

Levy, et al., "Effect of Ultrasound on Transdermal Drug Delivery to Rats and Guinea Pigs," *J. Clin. Invest.* 83:2074–2078 (1989).

Liu, et al., "Cotransport of Estradiol and Ethanol Through Human Skin In Vitro: Understanding the Permeant/Enhancer Flux Relationahip," *Pharmaceutical Research* 8:938–944 (1991).

Liu, et al., "Experimental Approach To Elucidate the Mechanism of Ultrasound–Enhanced Polymer Erosion and Release of Incorporated Substances," *Macromolecules* 25:123–128 (1992).

Machluf and Kost, "Ultrasonically enhanced transdermal drug delivery, Experimental approaches to elucidate the mechanism," *J. Biomater. Sci. Polymer Edn.* 5:147–156 (1993).

Mark, et al., "Oleic Acid Concentration and Effect in Human Stratum Corneum: Non–Invasive Determination by Attenuated Total Reflectance Infrared Spectroscopy In Vivo," *J. Controlled Rel.* 12:67–75 (1990).

Mitragotri, et al., "Ultrasound–Mediated Transdermal Protein Delivery," *Science* 269:850–853 (1995).

Mitragotri, et al., "A Mechanistic Study of Ultrasonically-–Enhanced Transdermal Drug Delivery," *J. Pharm. Sci.* 84:697–706 (1995).

Mitragotri, et al., *In Encl. of Pharm. Tech.*: Swarbrick and Bovlan, Eds., Marcel Dekker (1995)*.

Morimoto, Y., et al., "Prediction of Skin Permeability of Drugs: Comparison of Human and Hairless Rat Skin," *J. Pharm. Pharmacol.* 44:634–639 (1991).

Nagai and Konishi, "Buccaal/Gingival Drug Delivery Systems," *Journal of Controlled Release* (Elsevier Science Publishers B.V., Amsterdam) 6:353–360 (1987).

Newman, J., et al., "Hydrocortisone Phonophoresis," *J. Am. Pod. Med. Assoc.* 82:432–435 (1992).

Olanoff and Gibson, "Method to Enhance Intranasal Peptide Delivery," *Controlled Release Technology Pharmaceutical Application* (Lee, et al. Editors, American Chemical Society)301–309 (1987).

Ongpipattanankul, et al., "Evidence that Oleic Acid Exists in a Separate Phase Within Stratum Corneum Lipids," *Pharm. Res.* 8:350–354 (1991).

Parkin, et al., "Atopic manifestations in the acquired immune deficiency syndrome: response to recombinant interferon gamma," *Br. Med. J.*, 294:1185–1186 (1987).

Perry, et al., "Perry's Chemical Engineering Handbook" (McGraw–Hill, NY 1984).

Pishko, et al., "Amperometric Glucose Microelectrodes Prepared through Immobilization of Glucose Oxidase in Redox Hydrogels," *Anal. Chem.* 63:2268–2272 (1991).

Potts and Guv, "Predicting Skin Permeability," *Pharm. Res.* 9:663–669 (1992).

Bommer, et al., "Subcutaneous Erythropoeitin," *Lancet* 406 (1988).

Burnette, R. R., "Iontophoresis," *Transdermal Drug Delivery Developmental Issues and Research Initiatives* (Hadgraft and Guv, Editors, Marcel Dekker, 247–291, 1989).

Cleary, Gary W., "Transdermal Controlled Release Systems," *Medical Applications of Controlled Release* (Langer and Wise, Editors, CRCPress 203–251, 1984).

Clegg and Vaz, "Translational diffusion of proteins and lipids in artificial lipid bilayer membranes. A comparison of experiment with theory," *Progress in Protein–Lipid Interactions* Watts, ed. (Elsvier, NY 1985) Chapter 5:173–229.

Davis, J.,et al., "Characterization of Recombinant Human Erythropoietin Produced in Chinese Hamster Ovary Cells," *Biochemistry* 26:2633–2638 (1987).

Ebert, et al., "Transbuccal Absorption of Diclofenac Sodium in a Dog Model," *Controlled Release Technology Pharmaceutical Application* (Lee, et al. Editors, American Chemical Society)310–321 (1987).

TRANSDERMAL PROTEIN DELIVERY OR MEASUREMENT USING LOW-FREQUENCY SONOPHORESIS

This is a divisional of U.S. application Ser. No. 08/511,583 filed on Aug. 4, 1995, by Samir S. Mitragotri, Daniel Blankschtein and Robert S. Langer entitled "Transdermal Protein Delivery or Measurement Using Low-Frequency Sonophoresis," pending and a continuation in part of U.S. application Ser. No. 08/152,442 filed on Nov. 15, 1993, by Jonathan A. Eppstein, Deborah A. Eppstein, Joseph Kost and Robert S. Lunger entitled "Enhancement of Transdermal Monitoring Applications with Ultrasound and Chemical Enhancers", now U.S. Pat. No. 5,458,140.

BACKGROUND OF THE INVENTION

The present invention is generally in the area of drug delivery, and is particularly an improved method for transdermal drug delivery.

The United States government has rights in this invention by virtue of NIH grant GM44884 to R. Langer.

Transdermal drug delivery (TDD) offers several advantages over traditional delivery methods including injections and oral delivery. When compared to oral delivery, TDD avoids gastrointestinal drug metabolism, reduces first-pass effects, and provides sustained release of drugs for up to seven days, as reported by Elias, In *Percutaneous Absorption: Mechanisms-Methodology-Drag Delivery.*, Bronaugh, R. L., Maibach, H. 1. (Ed), pp 1–12, Marcel Dekker, New York, 1989. The word "transdermal", is used herein as a generic term. However, in actuality, transport of drugs occurs only across the epidermis where the drug gets absorbed in the blood capillaries. When compared to injections, TDD eliminates the associated pain and the possibility of infection. Theoretically, the transdermal route of drug administration could be advantageous in the delivery of many therapeutic proteins, because proteins are susceptible to gastrointestinal degradation and exhibit poor gastrointestinal uptake, proteins such as interferons are cleared rapidly from the blood and need to be delivered at a sustained rate in order to maintain their blood concentration at a high value, and transdermal devices are easier to use than injections.

In spite of these advantages, very few drugs and no proteins or peptides are currently administered transdermally for clinical applications because of the low skin permeability to drugs. This low permeability is attributed to the stratum corneum (SC), the outermost skin layer which consists of flat, dead cells filled with keratin fibers (keratinocytes) surrounded by lipid bilayers. The highly-ordered structure of the lipid bilayers confers an impermeable character to the SC (Flynn, G. L., In *Percutaneous Absorption: Mechanisms-Methodology-Drug Delivery.;* Bronaugh, R. L., Maibach, H. I. (Ed), pages 27–53, Marcel Dekker, New York, 1989). Several methods, which include chemical enhancers (Burnette, R. R. In *Developmental Issues and Research Initiatives;* Hadgraft J., G., R. H., Eds., Marcel Dekker: 1989; pp. 247–288) and electricity (Prausnitz *Proc. Natl. Acad. Sci.* USA 90, 10504–10508 (1993); Walters, K. A., in *Transdermal Drug Delivery: Developmental Issues and Research Initiatives,* Ed. Hadgraft J., Guy, R. H., Marcel Dekker, 1989), have been proposed to enhance transdermal drug transport. However, the efficacy of these methods in enhancing transdermal protein transport has been limited by the large protein size and relatively low electric charge on the proteins.

Ultrasound has been shown to enhance transdermal transport of low-molecular weight drugs (molecular weight less than 500) across human skin, a phenomenon referred to as sonophoresis (Levy, *J. Clin Invest.* 1989, 83, 2974–2078; Langer, R., In *"Topical Drug Bioavailability, Bioequivalence, and Penetration";* pp. 91–103, Shah V. P., M. H. I., Eds. (Plenum: New York, 1993); Frideman, R. M., *'Interferons: A Primer',* Academic Press, New York, 1981)). In a recent study of sonophoresis, it has been shown that application of ultrasound at therapeutic frequencies (1 MHz) induces growth and oscillations of air pockets present in the keratinocytes of the SC (a phenomenon known as cavitation). These oscillations disorganize the SC lipid bilayers thereby enhancing transdermal transport. However, application of therapeutic ultrasound does not induce transdermal transport of high-molecular weight proteins.

Transdermal drug delivery offers an advantageous alternative to oral delivery and injections. However, its applications are restricted to only a few drugs because of the extremely low skin permeability to drugs. A variety of approaches have been suggested to enhance transdermal transport of drugs. These include: i) use of chemicals to either modify the skin structure or to increase the drug concentration in the transdermal patch (Junginger, et al. In *"Drug Permeation Enhancement";* Hsieh, D. S., Eds., pp. 59–90 (Marcel Dekker, Inc. New York 1994); ii) applications of electric fields to create transient transport pathways [electroporation] or to increase the mobility of charged drugs through the skin [iontophoresis], and iii) application of ultrasound [sonophoresis].

U.S. Pat. Nos. 4,309,989 to Fahim and 4,767,402 to Kost, et al., disclose various ways in which ultrasound has been used to achieve transdermal drug delivery.

Sonophoresis has been shown to enhance transdermal transport of various drugs. Although a variety of ultrasound conditions have been used for sonophoresis, the most commonly used conditions correspond to the therapeutic ultrasound (frequency in the range of 1 MHz–3 MHz, and intensity in the range of 0–2 W/cm$^2$) (Kost, In Topical Drug Bioavailability Bioequivalence and Penetration, pp. 91–103, Maibach, H. I., Shah, V. P. (Ed) Plenum Press, New York, 1993; U.S. Pat. No. 4,767,402 to Kost, et al.). It is a common observation that the typical enhancement induced by therapeutic ultrasound is less than ten-fold. In many cases, no enhancement of transdermal drug transport has been observed upon ultrasound application. Accordingly, a better selection of ultrasound parameters is needed to induce a higher enhancement of transdermal drug transport by sonophoresis.

About 14 million people in the U.S. are currently suffering from diabetes of which about 1.5 million are treated by insulin administration the conventional treatment of diabetes involves checking blood glucose levels using finger pricking one or two times a day followed by injections of appropriate amounts of insulin. Although this method provides short term blood glucose control, it offers little patient compliance and results in high rates of long-term diabetic complications such as retinopathy, nephropathy and neuropathy. In order to minimize the long-term complications of diabetes, intensive treatment (insulin delivery three or more times a day accompanied by blood glucose measurements four or more times a day) has been suggested. It has been shown that an intensive treatment of diabetes resulted in about 75% decrease in the risk of developing retinopathy in diabetic patients compared to the conventional therapy. However, intensive treatment of diabetes is not practice by many patients due to pain and discomfort associated with multiple blood glucose measurements and insulin injections. Accordingly, development of a non-invasive blood glucose monitoring method would assist patients adopt intensive treatment.

It is therefore an object of the present to provide an improved, painless method for obtaining a patient sample for measurement of analytes in blood or other body fluids.

SUMMARY OF THE INVENTION

Applications of low-frequency (20 KHz) ultrasound enhances transdermal transport of high-molecular weight proteins.

It has been discovered that ultrasound can be used to measure the concentration of analytes in body fluids such as blood or lymph. Examples demonstrate measurement of blood glucose in vitro and in vivo.

BRIEF DESCRIPTION OF THE DRAWINGS

FIG. 2 is a graph of the glucose concentration extracted transdermally by sonophoresis at 20 KHz, 62.5 mW/cm$^2$, continuous, 1 minute) in vivo with the blood glucose level (mg/dl) of hairless rats.

DETAILED DESCRIPTION OF THE INVENTION

Figure 1A:
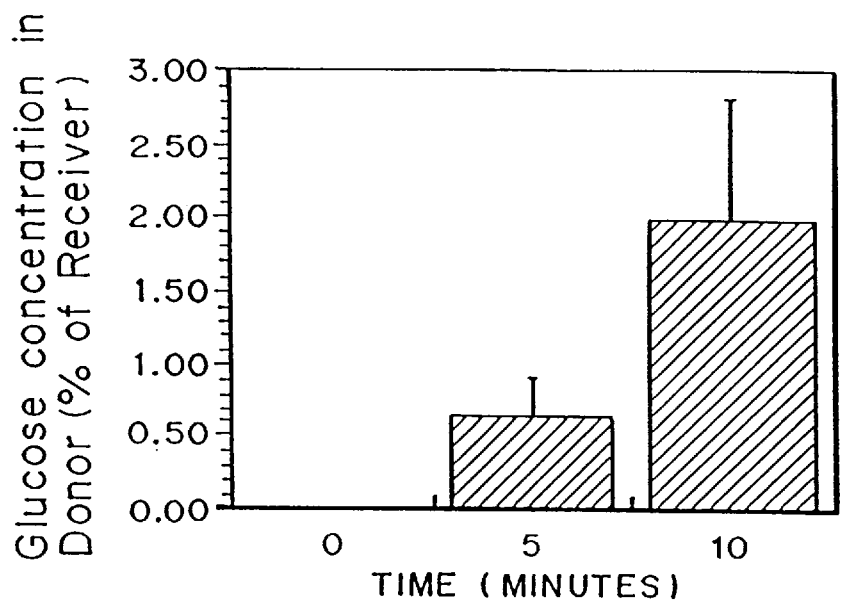
FIG. 1A is a graph of glucose concentration in the donor compartment (measured as percent of received glucose) over time (minutes) in an in vitro system.

Sonophoresis:

As used herein, sonophoresis is the application of ultrasound to the skin on which a drug, most preferably proteinaceous in nature, alone or in combination with a carrier, penetration enhancer, lubricant, or other pharmaceutically acceptable agent for application to the skin, has been applied. Ultrasound is defined as sound at a frequency of between 20 kHz and 10 MHz, with intensities of between greater than 0 and 3 W/cm$^2$. As used herein, "low frequency" sonophoresis is ultrasound at a frequency that is less than 1 MHz, more typically in the range of 20 to 40 KHz, which is preferably applied in pulses, for example, 100 msec pulses every second at intensities in the range of between zero and 1 W/cm$^2$, more typically between 12.5 mW/cm$^2$ and 225 mW/cm$^2$. Exposures are typically for between 1 and 10 minutes, but may be shorter and/or pulsed. The intensity should not be so high as to raise the skin temperature more than about one to two degrees Centigrade.

Many ultrasound devices are available commercially which can be used in the method described herein. For example, the ultrasonic devices used by dentists to clean teeth have a frequency of between about 25 and 40 KHz. Commercially available portable ultrasound tooth-brushes make use of a small sonicator contained within the toothbrush (Sonex International Corporation). This sonicator is portable and operates on rechargeable batteries. Small pocket-size sonicators carried by patients and used to "inject" drugs whenever required could be readily adapted from these devices. In addition, these devices could be potentially combined with sensors that can monitor drug concentrations in the blood to formulate a self-controlled drug (insulin, for example) delivery method that can potentially eliminate the attention required by the patient.

Devices typically used for therapeutic or diagnostic ultrasound operate at a frequency of between 1.6 and 10 MHz. These devices can also be modified for use at lower frequencies.

An optimal selection of ultrasound parameters, such as frequency, pulse length, intensity, as well as of non-ultrasonic parameters, such as ultrasound coupling medium, can be conducted to ensure a safe and efficacious application using the guidelines disclosed herein as applied by one of ordinary skill in the art.

Measurement of Analytes

Analytes to be Measured

A variety of analytes are routinely measured in the blood and/or lymph. Measurements usually require making a puncture in order to withdraw sample. Examples of typical analytes that can be measured include blood sugar (glucose), cholesterol, bilirubin, creatine, various metabolic enzymes, hemoglobin, heparin, vitamin K or other clotting factors, uric acid, carcinoembryonic antigen or other tumor antigens, and various reproductive hormones such as those associated with ovulation or pregnancy.

Measurement of Analytes

The ultrasound is applied to the skin at the site where the sample is to be collected. A reservoir or collecting container is applied to the site for collection of the sample, which is then measured using standard techniques. The ultrasound conditions are optimized as in the case for drug delivery, to maximize analyte recovery, while maintaining the relative levels of the analyte to other components of the sample.

The present invention will be further understood by reference to the following non-limiting examples.

EXAMPLE 1

Transdermal Glucose Extraction by Sonophoresis In Vitro.

Application of low-frequency ultrasound can be used to extract glucose across the skin, thus making non-invasive transdermal blood glucose monitoring potentially feasible.

Materials and Methods:

In Vitro Transdermal Transport Measurements:

Transdermal transport of a $^{14}$C labeled (New England Nuclear) as well as non-labeled (Sigma Chemicals) was studied in the presence as well as in the absence of low-frequency ultrasound. The permeability experiments were performed in vitro using human cadaver skin obtained from local hospitals. The skin was heat stripped by keeping the full-thickness skin in water at 60° C. for two minutes followed by the removal of the epidermis. The skin was then stored at 4° C. in a humidified chamber for up to 2 weeks. A piece of the epidermis was taken out from the chamber prior to the experiments and was mounted on a Franz diffusion cell (Crown Glass Co., FDC 200). The Franz diffusion cell consists of two compartments, the donor and the receiver compartments, with the stratum corneum facing the donor compartment. The skin was supported by a nylon mesh (Tetko, Inc.) to avoid any damage due to possible mechanical oscillations upon ultrasound application. The donor and receiver compartments were then clamped. The receiver compartment was filled Phosphate Buffer Saline (PBS, phosphate concentration=0.01M, NaCl concentration=0.137M) (Sigma Chemicals Co.) The donor compartment was filled with a solution of either radiolabelled glucose (1 mCi/ml) or non-labeled glucose (concentration in the range of 50 mg/dL to 300 mg/dL) in separate experiments. The concentration of the permeant in the receiver compartment was measured every 5 minutes using a scintillation counter (model 2000 CA, Packard) in the case of radiolabelled glucose and using a commercially available kit (Sigma Chemicals) in the case of unlabeled glucose.

Ultrasound was applied using a sonicator (VCX 400, Sonics and Materials) operating at a frequency of 20 KHz. The ultrasound intensity was measured using a hydrophone (Model 8106, Bruel and Kjaer).

Results

FIG. 1A shows the glucose concentration in the donor compartment (represented as percent of the glucose concentration in the receiver compartment) attained at different times during transdermal glucose extraction experiment. The figure shows that even a 5 minute ultrasound application (20 KHz, 125 mW/cm$^2$, continuous) results in a significant glucose transport across human skin in vitro. Specifically, the glucose concentration in the donor compartment after 5 minutes of sonophoresis is about 0.5% of that in the receiver compartment. After 10 minutes, the glucose concentration in the donor compartment was about 2% of that in the receiver compartment. The glucose concentration in this range can be measured in situ using glucose sensing electrodes, and can be calibrated to indicate actual blood glucose levels. The amount of glucose extracted by sonophoresis under a given condition varies in the case of skin obtained from different donors (typical variation 40% (SD)). However, the variation in the case of skin obtained from the same donor is only about 13%, thus indicating that it should be possible to achieve reliable estimates of glucose concentrations based on transdermal glucose extraction after performing calibration in vivo on the patient's skin.

Figure 1B:
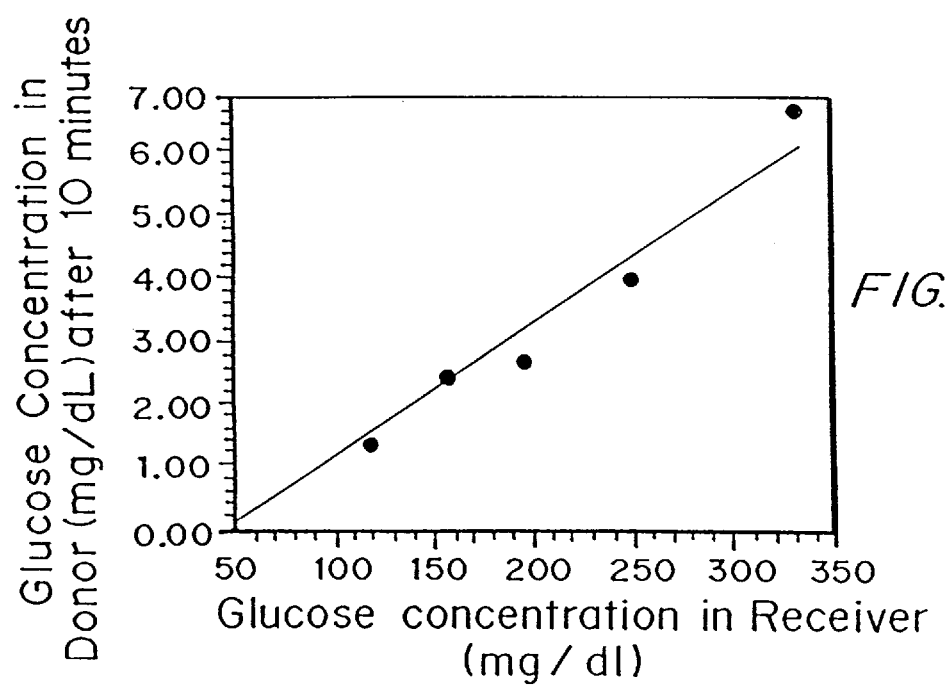
FIG. 1B is a graph of glucose concentration in the donor compartment (mg/dl) after ten minutes as a function of glucose concentration in the receiver compartment (mg/dl).
Figure 1C:
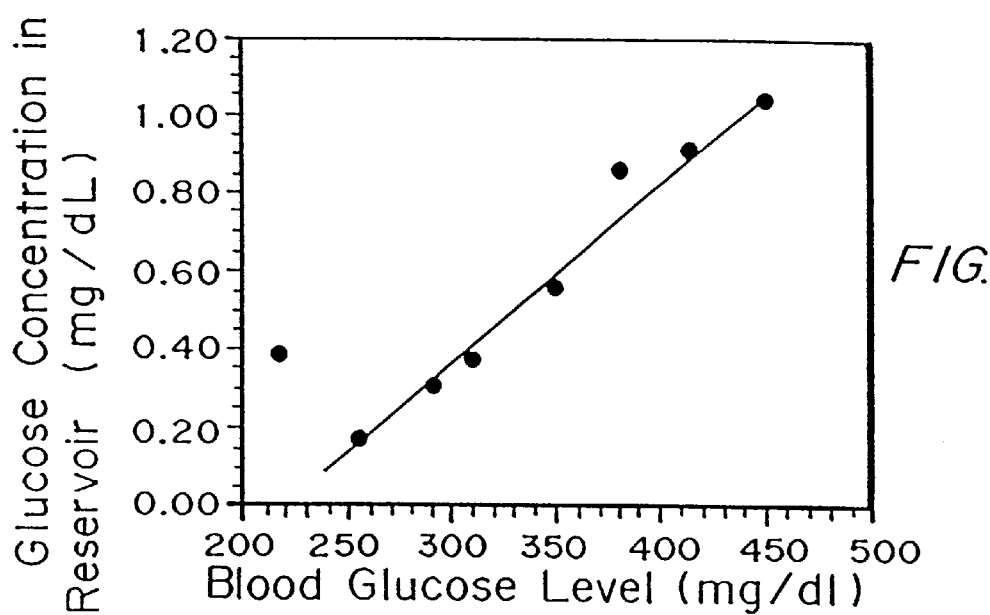

Additional experiments were performed to assess whether the amount of glucose transported by sonophoresis is proportional to the glucose concentration in the receiver compartment. In separate experiments, glucose concentration in the receiver solution was varied from 50 mg/dL to 350 mg/dL (typical variation in the blood glucose level of a diabetic patient) and performed sonophoresis using ultrasound (20 KHz, 125 mW/cm$^2$, continuous) for 10 minutes. FIG. 3B shows that the glucose concentration attained in the donor compartment 10 minutes after sonophoresis (represented as percentage of the glucose concentration in the receiver compartment) increased from 0.5 mg/dL to 6.5 mg/dL as glucose concentration in the receiver compartment increased from 50 mg/dL to 350 mg/dL. The line shown in FIG. 1B represents the best fit. These results show that the amount of glucose extracted across human skin is proportional to the glucose concentration under the skin, thus indicating that transdermal glucose extraction by sonophoresis could be potentially used for blood glucose measurement.

Example 2: Transdermal glucose extraction by sonophoresis in vivo.

Materials and Methods:

In Vivo Transport Experiments:

In vivo experiments were performed to assess the efficacy of sonophoresis across living skin. Hairless rats (Charles River, 8–12 weeks old, either sex) were used as an animal model for these studies, since it has been shown that the transport properties of hairless rat skin is comparable to that of human skin (Wester, *Animal Models for Percutaneous Absorption*, In *Topical Drug Bioavailability, Bioequivalence*, and Penetration, Shah V. P. and M. H. L., eds. (Plenum Press, NY 1993)). The hairless rats were anesthetized with a mixture of ketamine (60 mg/kg) and xylazine (10 mg/kg). After about an hour in anesthesia, a flanged glass cylinder (Crown Glass Company, diameter 20 mm, height 2 cm) was glued on the rat's back using a minimal amount of superglue (Permabond International) or vacuum grease (Dow Chemicals) on the outer edge of the flange. The center of the cylinder was located about 3 cm from the rear end of the rat. This particular site was chosen to avoid application of ultrasound directly on a sharp bone close to the body surface, which otherwise might have caused damage to the blood capillaries near the edge of the bone. The cylinder was filled with PBS (phosphate concentration =0.01M, NaCl concentration=0.137M) (Sigma Chemicals Co.). Ultrasound (20 KHz, 125 mW/cm$^2$, continuous) was applied for 1 minute by immersing the transducer in the donor solution. The concentration of glucose in PBS was measured using an assay kit (Sigma Chemicals).

Results:

In vivo experiments were performed using normal as well as diabetic hairless rats to assess whether low-frequency ultrasound extracts glucose across living skin. FIG. 2 shows that application of ultrasound (20 KHz, 62.5, continuous, 1 minute, applied on side of the stomach) induces glucose extraction by an amount proportional to the rat blood glucose level. Specifically, the glucose concentration in the reservoir after extraction increased from 0.2 mg/dL to 1 mg/dL as the rat blood glucose level increased from about 200 mg/dL to 450 mg/dL in separate experiments. These results indicate that calibration curves relating glucose extracted transdermally and blood glucose level can be used for non-invasive blood glucose measurements.

Modifications and variations of the method for transdermal analyte enhancement using sonophoresis described herein will be obvious to those skilled in the art and are intended to be encompassed by the following claims.

We claim:

1. A method for collecting an analyte to be measured in a blood or lymph sample comprising applying at an appropriate site for collection of a blood or lymph sample an effective amount of ultrasound at a frequency between 20 kH and 1.5 MHz to extract analyte in the absence of penetration enhancers and collecting the blood or lymph sample at the site where the ultrasound is applied.

2. The method of claim 1 wherein the ultrasound is applied at an intensity of between 0 and 3 W/cm$^2$.

3. The method of claim 2 wherein the ultrasound is applied at a frequency between 20 kHz and 45 kHz.

4. The method of claim 1 wherein the intensity is between zero and 1 W/cm$^2$.

5. The method of claim 1 wherein the analyte is collected into a reservoir.

6. The method of claim 1 wherein the ultrasound is administered to make a puncture in the skin for withdrawal of analyte.

7. The method of claim 1 wherein the ultrasound is administered in pulses.

* * * * *